United States Patent [19]
Mylari et al.

[11] Patent Number: 5,182,391
[45] Date of Patent: Jan. 26, 1993

[54] PROCESS AND INTERMEDIATES FOR THE PREPARATION OF OXOPHTHALAZINYL ACETIC ACIDS AND ANALOGS THEREOF

[75] Inventors: Banavara L. Mylari, Waterford; William J. Zembrowski, Oakdale, both of Conn.

[73] Assignee: Pfizer Inc., New York, N.Y.

[21] Appl. No.: 906,778

[22] Filed: Jun. 30, 1992

Related U.S. Application Data

[62] Division of Ser. No. 768,784, Sep. 30, 1991, which is a division of Ser. No. 540,000, Jun. 15, 1990, Pat. No. 5,075,442, which is a division of Ser. No. 350,997, May 11, 1989, Pat. No. 4,954,269.

[51] Int. Cl.$^5$ ................ C07D 519/00; C07D 417/06; C07D 487/04; C07D 471/04
[52] U.S. Cl. ................................................ 544/236
[58] Field of Search ........................................ 544/236

[56] References Cited

U.S. PATENT DOCUMENTS 5,034,051  7/1991  Kune ................................... 544/236

Primary Examiner—Mark L. Berch
Attorney, Agent, or Firm—Peter C. Richardson; Paul H. Ginsburg; Gezina Holtrust

[57] ABSTRACT

Oxophthalazinyl acetic acids having benzothiazole side chains are prepared by reacting an oxophthalazinyl thioacetamide acetate with hydrogen sulfide and a nitrophenyl compound having a reactive group such that the benzothiazole side chain may be formed by ring closure involving the thioacetamide group. The oxophthalazinyl thioacetamide may be prepared by reacting the corresponding cyanomethyloxophthalazinyl acetate with hydrogen sulfide in the presence of tertiary amines. Analogous indazole and oxopyridopyridazinone acetic acids may be prepared similarly, as well as oxophthalazinyl, indazole and oxopyridopyridazinone acetic acids having thiazoloyridinyl side chains.

1 Claim, No Drawings

PROCESS AND INTERMEDIATES FOR THE PREPARATION OF OXOPHTHALAZINYL ACETIC ACIDS AND ANALOGS THEREOF

This is a division of application Ser. No. 768,784 filed on Sep. 30, 1992 which is a divisional of application Ser. No. 540,000, filed on Jun. 15, 1990 now U.S. Pat. No. 5,075,442, which is a divisional of application Ser. No. 350,997 filed on May 11, 1989, now U.S. Pat. No. 4,954,269.

BACKGROUND OF THE INVENTION

The present invention relates to processes and intermediates for the preparation of oxophthalazinyl acetic acids and analogues thereof. The latter compounds are aldose reductase inhibitors and are useful in preventing or alleviating chronic complications associated with diabetes.

Aldose reductase inhibitors that may be prepared by the processes of the present invention are disclosed in United States Ser. No. 07/263,577, filed Oct. 27, 1988 and European Patent Application Publication Number 222576. Nitriles that are used as starting materials in the processes of the present invention are disclosed in European Patent Application Publication Number 0295051.

West German Patent Application DE 3337859 refers to preparation of benzothiazole derivatives by cyclization of 2-substituted aniline or nitrobenzene compounds with thioamide derivatives.

International Application PCT/US88/00110, filed Jan. 19, 1988 refers to 1H-indazole-3-acetic acids as aldose reductase inhibitors.

SUMMARY OF THE INVENTION

The present invention relates to a process for preparing a compound of the formula

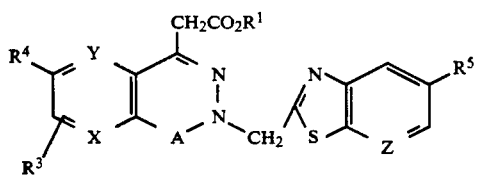

wherein X and Y are independently CH or N; Z is N or $CR^6$; A is a covalent bond or C=O; $R^1$ is $C_1$-$C_6$ alkyl; $R^3$ and $R^4$ are the same or different and are hydrogen, fluoro, chloro, bromo, trifluoromethyl, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, or nitro, or $R^3$ and $R^4$ taken together are $C_1$-$C_4$ alkanedioxy; and $R^5$ and $R^6$ are the same or different and are hydrogen, fluoro, chloro, bromo, trifluoromethyl, nitro, cyano, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, trifluoromethyl, trifluoromethoxy, or trifluoroacetyl, with the proviso that when X or Y is N, then $R^3$ and $R^4$ are the same or different and are hydrogen, $CF_3$ or $C_1$-$C_4$ alkyl, which comprises reacting a compound of the formula

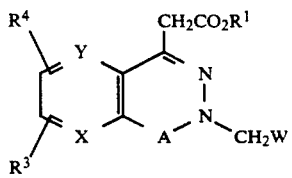

wherein W is

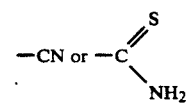

and X, Y, A, $R^1$, $R^3$ and $R^4$ are as defined above, with a compound of the formula

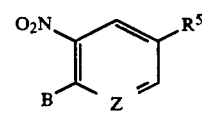

wherein Z and $R^5$ are as defined above, and B is F, Cl, Br, I, SCN or $OSO_2R^7$ wherein $R^7$ is $C_1$-$C_4$ alkyl, phenyl, methylphenyl, nitrophenyl or bromophenyl, in the presence of hydrogen sulfide, with the proviso that when W is CN, the reaction is conducted in the presence of a tertiary amine.

Substituents $R_3$ and $R_4$ when other than trifluoromethyl or $C_1$-$C_4$ alkyl can not be directly across or immediately flanked by X or Y when they are nitrogen.

In a preferred embodiment of the invention, the reaction is also conducted in the presence of a tertiary amine when W is

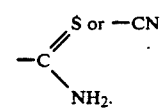

The present invention also relates to a compound of the formula

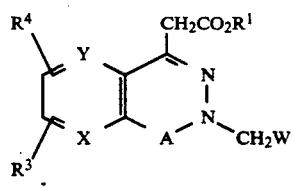

wherein W is

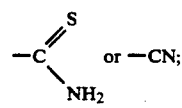

$R^1$ is $C_1$-$C_6$ alkyl; $R^3$ and $R^4$ are the same or different and are hydrogen, fluoro, chloro, bromo, trifluoromethyl, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, or nitro, or $R^3$ and $R^4$ taken together are $C_1$-$C_4$ alkanedioxy; and X and Y are independently CH or N, and A is a covalent bond or C=O, with the proviso that when X or Y is N, then $R^3$ and $R^4$ are the same or different and are trifluoromethyl or $C_1$-$C_4$ alkyl, and with the proviso that when W is CN and A is C=O, then X and Y are not both CH.

The invention further relates to a compound of the formula

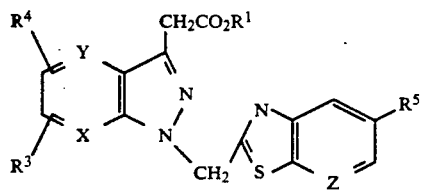

wherein X and Y are independently CH or N; Z is N or $CR^6$; $R^1$ is $C_1$-$C_6$ alkyl; $R^3$ and $R^4$ are the same or different and are hydrogen, trifluoromethyl, or $C_1$-$C_4$ alkyl; and $R^5$ and $R^6$ are the same or different and are hydrogen, fluoro, chloro, bromo, trifluoromethyl, nitro, cyano, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, trifluoromethylthio, trifluoromethoxy, or trifluoroacetyl; with the proviso that X and Y are not both CH.

Also included in the invention are a composition for inhibition of aldose reductase activity comprising a compound of formula VI in an amount effective in the inhibition of aldose reductase activity, in admixture with a pharmaceutically acceptable carrier; and a method of inhibiting aldose reductase activity comprising administering to a diabetic host an effective amount of a compound of formula VI.

DETAILED DESCRIPTION OF THE INVENTION

The processes of the present invention are illustrated in Scheme I.

The compound of the formula IIB is reacted with the compound of the formula III to prepare a compound of the formula I. Generally, the reaction is conducted in a polar solvent. Suitable solvents include sulfolane (tetrahydrothiophene-1,1-dioxide), pyridine, diethylene glycol dialkyl ethers (e.g. diethylene glycol diethyl ether), N-methyl pyrrolidone, and mixtures thereof. The preferred solvent is dimethylformamide. The reaction temperature is generally between about 110° C. and about 180° C., preferably the reflux temperature of the solvent. The reaction pressure is not critical. Generally, the pressure will range from about 0.5 to about 2 atmospheres, and will preferably be ambient pressure (i.e. about one atmosphere). The compound of formula IIB when W is CN is reacted with the compound of the formula III in the presence of a tertiary amine. Suitable tertiary amines are tri($C_2$-$C_6$)alkylamines, e.g. triethyl amine.

The compound of the formula I may be hydrolyzed in aqueous base to prepare a compound of the formula V.

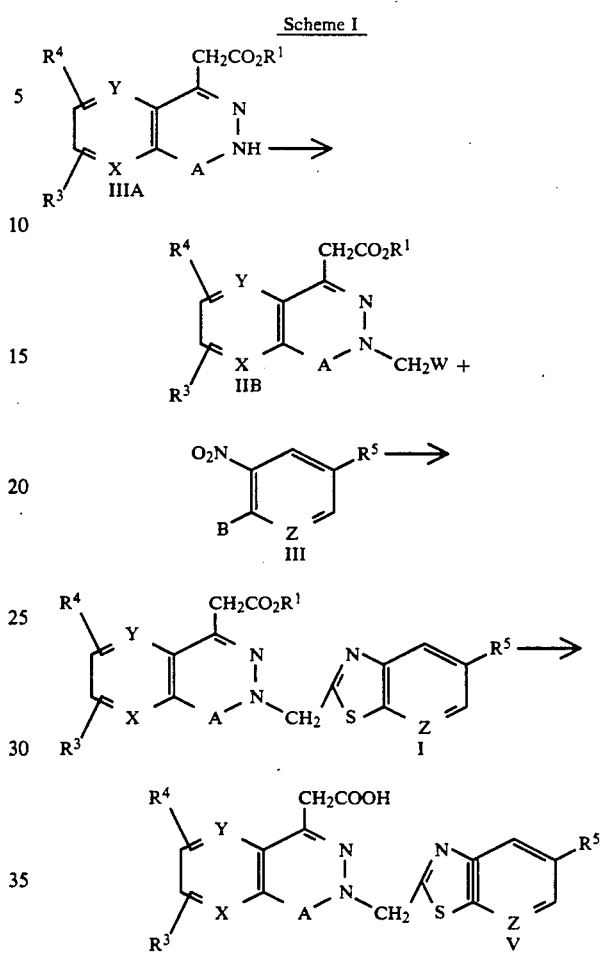

When $R^1$ is tertiary butyl, the hydrolydes to a compound of the formula V is more conviently performed in concentrated sulfuric acid or trifluoroacetic acid.

The compound of the formula IIB wherein W is cyano may be prepared by reacting a compound of the formula IIA with a compound of the formula L—$CH_2CN$ wherein L is chloro, bromo, —$OSO_2$(-$C_1$-$C_4$ alkyl), or —$OSO_2$aryl wherein aryl is phenyl or naphthyl optionally substituted by $C_1$-$C_4$ alkyl, halogen, or nitro, in the presence of a base. Examples of suitable bases include alkali metal hydride such as sodium hydride, alkali metal carbonates such as potassium carbonate, alkali metal hydroxides such as sodium or potassium hydroxide, and alkali metal alkoxides such as potassium tertiary butoxide and sodium methoxide. The reaction may be conducted in a solvent which is inert under the reaction conditions. Suitable solvents are inert solvents such as dimethylformamide, dimethylacetamide, acetone, and diglyme. The reaction is generally at temperatures of between about 0° C. and about 100° C. Preferably, the reaction temperature is between about 40° to 60° C.

The compound of the formula IIB wherein W is —C(S)$NH_2$ may be prepared by reacting a compound of the formula IIB wherein W is CN with hydrogen sulfide in the presence of tertiary amines such as tri(C-2-$C_6$)alkyl amines, e.g. triethyl amine, in the presence of a solvent such as pyridine or dimethylformamide. Preferably, the reaction is conducted in dimethylformamide. Generally, the reaction is conducted at temperatures between about ambient temperature and about 100° C. Preferably, the reaction temperature is between about 40° and 60° C.

The novel compounds of formula V and the pharmaceutically acceptable salts thereof are useful as inhibitors of the enzyme aldose reductase in the prevention and alleviation of chronic complications of diabetes, such as diabetic cataracts, retinopathy, nephropathy and neuropathy. The compound may be administered to a subject in need of treatment by a variety of conventional routes of administration, including orally, parenterally and topically. In general, these compounds will be administered orally or parenterally at dosages between about 0.5 and 25 mg/kg body weight of the subject to be treated per day, preferably from about 1.0 to 10 mg/kg. However, some variation in dosage will necessarily occur depending on the condition of the subject being treated. The compound may be administered alone or in combination with pharmaceutically acceptable carriers, in either single or multiple doses. Pharmaceutical compositions formed by combining a novel compound of the formula I or a pharmaceutically acceptable salt thereof and pharmaceutically acceptable carriers may be administered in a variety of dosage forms such as tablets, powders, lozenges, syrups, and injectable solutions.

Compounds of formula I and pharmaceutically acceptable salts thereof may also be employed for the treatment of diabetic cataracts by topical administration. The ophthalmic preparation will contain a compound of formula I or a pharmaceutically acceptable salt thereof in a concentration from about 0.01 to about 1% by weight, preferably from about 0.05 to about 0.5% by weight, in a pharmaceutically acceptable solution, suspension or ointment. Some variation in concentration will necessarily occur, depending on the particular compound employed and the condition of the subject to be treated.

The activity of the compounds of formula VI of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e. diabetic, rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; (5) measuring their ability to delay cataract formation and reduce the severity of lens opacities in chronic galactosemic rats; (6) measuring their ability to prevent sorbitol accumulation and cataract formation in isolated rat lens inclubated with glucose; and (7) measuring their ability to reduce already elevated sorbitol levels in isolated rat lens incubated with glucose.

The following Examples illustrate the processes of the present invention. All melting points are uncorrected.

EXAMPLE 1

Ethyl-3-thioacetamido-4-oxo-phthalzin-1-ylacetate

Hydrogen sulfide was bubbled through a solution of ethyl-3-cyanomethyl-4-oxo-phthalazin-1-ylacetate (54.2 g) in dimethylformamide (200 ml) containing triethyl amine (1 ml) maintained at 60° C. After 15 minutes, the hydrogen sulfide bubbling was discontinued and heating was continued for 2 hours. The solution was cooled to room temperature and then poured slowly over ice-water (2000 ml). The granulated thick precipitate was filtered, washed with water (2×200 ml) and then air-dried to obtain the title compound (yield 57.8 g; m.p. 149°–151° C.).

EXAMPLE 2

Ethyl-3-(5-trifluoromethylbenzothiazol-2-ylmethyl)-4-oxo-3-H-phthalazin-1-ylacetate Procedure A A solution of ethyl-3-cyanomethyl-4-oxophthalazin-1-ylacetate (10.84 g) and a catalytic amount of triethylamine (0.2 g) in dimethylformamide (40 ml) maintained at 50°–55° C. was bubbled with hydrogen sulfide for 15 minutes. After hydrogen sulfide bubbling was discontinued, the reaction was continued for 3 hours. At this stage, the solution was resaturated with hydrogen sulfide and 4-chloro-3-nitrobenzotrifluoride (9.47 g) was added to the reaction mixture. The reaction mixture immediately turned light orange in color and it was then heated to 140° C. for 2.5 hours. The solution was cooled to room temperature and then was added dropwise to a mixture of ice-water and ethanol (800 ml; 4:1). The pH of the aqueous ethanol was adjusted to about 2.0 with a few drops of 6N hydrochloric acid. The resulting granulated solid was filtered and the residue was crystallized from a 3:1 mixture of ethanol-methylene chloride (50 ml). The solid was collected by filtration and was then air-dried to obtain the title compound (yield 12.2 g). The mother liquor contained an additional quantity (analytical estimate, about 1.0 g) of the title compound.

Procedure B

To a solution of ethyl-3-thioacetamido-4-oxophthalazin-1-ylacetate (6.1 g) in dimethylformamide (30 ml) saturated with hydrogen sulfide was added 4-chloro-3-nitrobenzotrifluoride (4.5 g) and the resulting solution was heated slowly to reflux. When the reflux temperature was reached, a slow current of hydrogen sulfide was passed through the solution and the refluxing continued for 4 hours. The reaction mixture was then cooled and poured onto ice-water (500 ml). The resulting gum was separated by decantation and then triturated with ethanol (75 ml). The granulated light yellow solid was filtered and the precipitate was collected and crystallized from ethanol (200 ml) to obtain the title compound (yield 4.1 g).

In a similar manner was prepared ethyl-3-(7-chlorobenzothiazol-2-ylmethyl)-4-oxo-3H-phthalazin-1-ylacetate, m.p. 119° C. and ethyl-3-(5-chloro-7-fluorobenzothiazol-2-ylmethyl)-4-oxo-3-H-phthalazine-1-yl-acetate, m.p. 202°–204° C. using 2,3-dichloronitrobenzene and 2,5-dichloro-3-fluoro-nitrobenzene, respectively, in place of 4-chloro-3-nitrobenzotrifluoride.

EXAMPLE 3

I. Methyl 1H-Indazole-3-ylacetate

A solution of 1H-indazole-3-acetic acid (1.0 g) prepared according to J. Am. Chem. Soc., 79, 5245 (1957), in methanol (30 ml) containing five drops of concentrated sulfuric acid was refluxed for 8 hours. The reaction mixture was then concentrated to a low volume and diluted with ethyl acetate (20 ml). The organic layer was washed with water (2×10 ml) and then with sodium bicarbonate solution (10 ml, 10%). The ethyl acetate layer was collected and then dried to obtain the title compound (yield: 0.8 g; m.p. 146° C.).

II. Methyl-(1-cyanomethyl)-1-H-indazole-3-ylacetate

To a solution of methyl-1-H-indazole-3-ylacetate (1.9 g) in dimethylformamide (4 ml) was added sodium hydride (0.58 g; 50% by weight dispersed in oil) and the mixture stirred for 15 minutes at room temperature. Chloroacetonitrile (1.9 g) dissolved in dimethylformamide (2 ml) was then added and the reaction mixture stirred for 6 hours. The mixture was then poured onto ice-water (20 ml), the pH was adjusted to about 3 by the addition of sufficient dilute HCl, and the resulting precipitate was collected and air-dried (yield 1.87 g) m.p. 128°–134° C.

EXAMPLE 4

3-(7-Chlorobenzothiazol-2ylmethyl)-4-oxo-3-H-phthalazin-1-ylacetic acid

To a solution of ethyl-3-(7-chlorobenzothiazol-2-ylmethyl)-4-oxo-3-H-phthalazin-1-ylacetate (800 mg) in a 2:1 mixture of ethanol and tetrahydrofuran (30 ml) was added 5 ml of 1% aqueous potassium hydroxide solution and the mixture was stirred at room temperature for 2 hours. The reaction mixture was concentrated by evaporation under vacuum and the resulting residue was diluted with water (10 ml). Upon adjusting the pH of the solution to around 2 with sufficient 10% HCl, a white precipitate was obtained. The precipitate was collected by filtration, air-dried and then crystallized from methylene chloride (10 ml) to obtain the title compound (yield, 273 mg), m.p. 168° C.

Similarily, ethyl-3-(5-chloro-7-fluoro-benzothiazol-2-ylmethyl)-4-oxo-3-H-phthalazin-ylacetate was hydrolyzed to 3-(5-chloro-7-fluoro-benzothiazol-2-ylmethyl)-4-oxo-3-H-phthalzanin-1-ylacetic acid (m.p. 207°–207.5° C.).

EXAMPLE 5

I. 3-Oxo-pyrido[3,2-c] and 3-oxo-pyrido[2.3-c]furan-1-ylidene acetic acid t-butyl ester A mixture of the commercially available 2,3-pyridinedicarboxylic anhydride (29.8 g), (t-butoxycarbonylmethylene)triphenyl phosphorane (75.2 g) and methylene chloride (1000 ml) was stirred at room temperature for 60 hours. The mixture was evaporated to dryness and the residue chromatographed over silica gel (2.0 kg). Upon careful elution with a solution of methylene chloride in ethyl acetate (49:1) and monitoring of the eluent fractions by thin layer chromatography, two products were isolated. The less polar product designated A was identified as a mixture (1:1) of E or Z 3-oxo-pyrido[2,3-c]furan-1-ylidene acetic acid t-butyl ester [¹H NMR(CDCl₃, 250 MHz); 1.5 (s, 9H), 6.1 (s, 1H), 7.8 (dd, J=6 Hz, 1H), 8.40 (dd, J₁=6 Hz, J₂=Hz, 1H), 9.1 (dd, J₁=6H, J₂=1H, 1H) and E 3-oxo-pyrido[3,2-c)furan-1-ylidene acetic acid t-butyl ester [¹H NMR(CDCl₃, 250 MHz): 1.5 (s, 9H), 6.2 (s, 1H), 7.9 (dd, J=6 Hz, 1H), 9.0 (dd, J=6 Hz, 1H), 9.2 (d, J=12 Hz, 1H).

The more polar product designated B was identified as a mixture (about 1:10) of E 3-oxo-pyrido[3,2-c]furan-1-ylidene acetic acid t-butyl ester and E or Z 3-oxo-pyrido [2,3-c]furan-1-ylidene acetic acid t-butyl ester. The less polar product A was not separated into pure components. The more polar product B was rechromatographed over silica gel (500 g) and eluted with a solution of methylene chloride in ethyl acetate (9:1). Evaporation of the early fractions gave pure E 3-oxo-pyrido[3,2-c]furan-1-ylidene acetic acid t-butyl ester (1.8 g, m.p. 113°–114° C.). Evaporation of the later fractions gave pure E or Z 3-oxo-pyrido[2,3-c]furan-1-ylidene acetic acid t-butyl ester (11.5 g, m.p. 118° C.).

II. t-Butyl 8-oxo-7H-pyrido[2,3-d]pyridazine-5-yl acetate

To a solution of E 3-oxo-pyrido[3,2-c]furan-1-ylidene acetic acid t-butyl ester (1.85 g) in ethanol (10 ml) was cautiously added hydrazine hydrate (1.3 ml) and the mixture was then gently refluxed for 1 hour. The solution was concentrated to remove ethanol and the residue was diluted with water (20 ml). Sufficient 10% HCl was then added to adjust the pH to about 2.0. The precipated solid was collected and the collected solid was air-dried (1.36 g, m.p. 186°–188° C.).

EXAMPLE 6

I. t-Butyl 5-oxo-6H-pyrido[2,3-d]pyridazine-8-yl acetate

To a solution of E or Z 3-oxo-pyrido[2,3-c]furan-1-ylidene acetic acid t-butyl ester (m.p. 118° C.; 10.0 g) in ethanol (25 ml) was added hydrazine hydrate (10 ml) dropwise and the resulting solution was refluxed for 10 minutes. The solution was evaporated to remove ethanol, the residue was diluted with water (20 ml) and sufficient 10% HCl was added to adjust the pH to about 6. The precipitated solid was filtered and the collected solid was air-dried (8.9 g, m.p. 178°–179° C.).

II. t-Butyl 6-(5-trifluoromethylbenzothiazole-2-yl-methyl)-5-oxo-6H-pyrido[2,3-d]pyridazine-8-ylacetate To a solution of t-butyl 5-oxo-6H-pyrido[2,3-d]pyridazine-8-yl acetate (0.5 g) in dimethylformamide (5 ml) containing potassium t-butoxide (0.25 g) was added 5-trifluoromethyl-2-chloromethylbenzothiazole (0.55 g). The solution was stirred at room temperature overnight and then poured over ice-water (20 ml); sufficient 10% HCl was added to adjust the pH to about 5.0 and the precipitated crude solid was collected. The solid was chromatographed over silica gel using a 1:1 mixture of methylene chloride and ethyl acetate as eluent to obtain the product (0.66 g, m.p. 121°–122° C.).

What is claimed is:

1. A compound of the formula

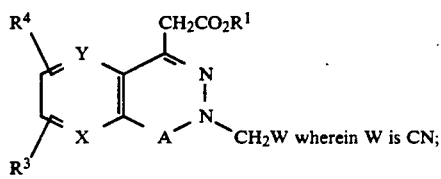

wherein W is CN;

R¹ is C₁–C₆ alkyl; R³ and R⁴ are the same or different, and are trifluoromethyl, or C₁–C₄ alkyl; one of X and Y is CH and the other is N, and A is C=O.

* * * * *